(12) United States Patent
Arai et al.

(10) Patent No.: US 6,319,193 B1
(45) Date of Patent: Nov. 20, 2001

(54) AUXILIARY DEVICE FOR PULSATILE CORONARY ARTERY BYPASS

(75) Inventors: Hirokuni Arai, Nakano; Haruhiko Masuda, Akita, both of (JP)

(73) Assignee: Sumitomo Bakelite Company LTD, Tokyo (JP)

( * ) Notice: Subject to any disclaimer, the term of this patent is extended or adjusted under 35 U.S.C. 154(b) by 0 days.

(21) Appl. No.: 09/485,059

(22) PCT Filed: Jun. 3, 1999

(86) PCT No.: PCT/JP99/02977

§ 371 Date: Feb. 3, 2000

§ 102(e) Date: Feb. 3, 2000

(87) PCT Pub. No.: WO99/63895

PCT Pub. Date: Dec. 16, 1999

(30) Foreign Application Priority Data

| Jun. 5, 1998 | (JP) | 10-157202 |
| Jul. 6, 1998 | (JP) | 10-190478 |
| Aug. 20, 1998 | (JP) | 10-233736 |
| Jan. 27, 1999 | (JP) | 11-018705 |

(51) Int. Cl.⁷ ............... A61F 2/00; A61F 13/00
(52) U.S. Cl. .................................................. 600/37
(58) Field of Search .................. 600/37, 207, 208, 600/210, 215; 606/153, 151, 192; 623/1; 601/151; 128/898

(56) References Cited

U.S. PATENT DOCUMENTS

| 3,665,926 | 5/1972 | Flores . |
| 4,058,126 | 11/1977 | Leveen . |
| 4,106,508 | 8/1978 | Berlin . |
| 5,735,791 * | 4/1998 | Alexander, Jr. et al. .............. 600/37 |
| 5,976,178 * | 11/1999 | Goldsteen et al. ....................... 623/1 |
| 6,036,640 * | 3/2000 | Corace et al. ........................ 600/207 |
| 6,110,187 * | 8/2000 | Donlon ................................. 606/151 |

FOREIGN PATENT DOCUMENTS

| 0791330A2 | 8/1997 | (EP) . |
| 297 08 050U1 | 8/1997 | (DE) . |
| 4-309337 | 10/1992 | (JP) . |
| 10-14928 | 1/1998 | (JP) . |
| 10-118079 | 5/1998 | (JP) . |
| 10-5230 | 7/1998 | (JP) . |

OTHER PUBLICATIONS

Australian Patent Office Search Report, Application No. SG 0000507–4, dated Jul. 7, 2000.

* cited by examiner

Primary Examiner—John P. Lacyk
Assistant Examiner—Brian Szmal
(74) Attorney, Agent, or Firm—Smith, Gambrell & Russell, LLP

(57) ABSTRACT

The present invention provides a device for safely and completely performing the anastomosis of the bypass graft to the coronary artery on the beating heart with good patency, which comprises:

- a means for rotating a heart to obtain excellent exposure of the target coronary artery to be anastomosed and absorbing the portion of the myocardium to stabilize the anastomosis area without reducing cardiac output;
- a means for perfusion to the distal myocardium during the anastomosis of the bypass graft to the coronary artery; and
- a means for compressing the coronary artery proximal and distal to the site of the anastomosis at a minimum stress to perform occlusion for obtaining bloodless operative field.

8 Claims, 9 Drawing Sheets

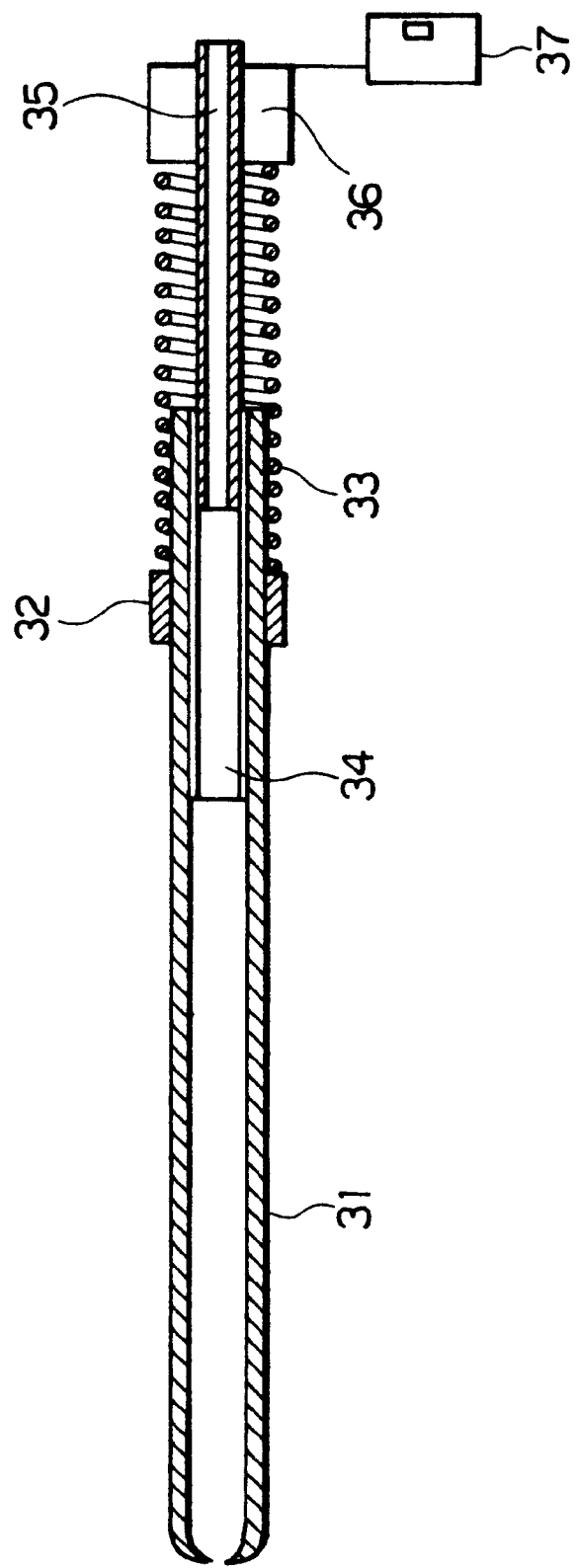
FIG. 8 (a)
FIG. 8 (b)
FIG. 8 (c)

AUXILIARY DEVICE FOR PULSATILE CORONARY ARTERY BYPASS

TECHNICAL FIELD

The present invention relates to a device used for performing the anastomosis of a bypass graft to the coronary artery on the beating heart.

BACKGROUND OF THE INVENTION

In recent years, interventional treatments, such as percutaneous transluminal angioplasty or stent placement for coronary stenosis, have been widely applied for patients who suffer from ischemic heart disease such as myocardial infarction. Interventional treatments provide shorter post-treated hospital stays to patients because methods of these treatments are less invasive to patients. However, patients must receive observations over a long time after hospital stays because restenosis often occurs.

Meanwhile, coronary artery bypass grafting (hereinafter abbreviated to CABG) has been applied for patients. CABG procedures comprise exposing the heart, and performing the anastomosis of the bypass graft to the distal portion of the coronary stenosis to provide blood flow to distal coronary artery. This method offers many advantages to patients in terms of potential for no restenosis in the postoperative period.

CABG, is applicable to many of patients who have some risk factors to the interventional treatment. Risk factors are, for example, restenosis in the post-treated period of interventional treatments, serious heart failure, occlusions or stenosis in a plurality of coronary arteries, calcification in ascending aorta, chronic diseases in brain, kidney, respiratory system and/or the like, and advancing age of patients. But all of theme risk factors to interventional treatments are also risk factors to CABG with cardiopulmonary bypass. Cardiopulmonary bypass has allowed all surgeons to perform the operation with good patency rate, but deleterious effects of cardiopulmonary bypass to patients who have those risk factors are wall documented. In fact, those patients have been abandoned.

If anesthesia and medial sternotomy are able to be applied to those patients mentioned above, CABG procedures would be performed on the beating heart without cardiopulmonary bypass and cardiac arrest. This less invasive technique is called off pump CABG (hereinafter abbreviated to OPCAB) and becoming increasingly popular in terms of a means for saving such an abandoned patient. The anastomosis of the bypass graft is performed under temporary proximal and/or distal occlusion of target coronary artery to provide a bloodless operative field.

Further, the least invasive technique called minimally invasive direct coronary artery bypass grafting (hereinafter abbreviated to MIDCAB) is applied to patients. The procedures of this technique are performed on the beating heart with left or right anterior small thoracotomy and no medial sternotomy. in the case of CABG with medial sternotomy for obtaining exposure of the coronary artery, patients were obliged to stay in hospital for about one month or more and suffered from postoperative pain. In the case of MIDCAB with anterior small thoracotomy, however, patients would take no pain and have good recovery so that they are able to take a meal on the next day after the operation. Thus, MIDCAB offers many advantages to patients in terms of shorter postoperative hospital stays, cost savings, and superior postoperative appearance resulting from decreasing trauma.

In OPCAB and MIDCAB procedures, it is difficult to perform completely the anastomosis of the bypass graft with good patency rate to the target coronary artery in a short time because the heart is beating. In order to resolve the problem, two types of devices for target area stabilization are developed and are in use. One is a compression type stabilizer, and the other is a suction type tissue stabilizer.

The compression type stabilizer comprises, as described in, for example, JP-A-10-5203, an arm and fork-shaped two legs attached at the front end of the arm. The shape and the number of legs are not restricted thereto. While the arm is fixed to a sternum retractor, the two legs compress the target area and restrict the motion of the myocardium. In fact, cardiac output has decreased as the result of direct ventricular compression with reduced stroke.

The suction type tissue stabilizer, an described in, for example, U.S. Pat. No. 5,727,569, immobilizes the target area by providing a sucker to the surface of the target area, attaching the surface to the sucker, and pulling the sucker with the tissue of the heart. However, internal bleeding has been observed in the tissue of the heart surface after operation as the result of suction of tissue at the vacuum pressure of about −350 mmHg. Since the size of the sucker is large, the operative field becomes too small to perform MIDCAB procedure with anterior small thoracotomy.

In OPCAB procedure, it is necessary to rotate the heart to obtain good exposure of the target coronary artery. In the case of obtaining proper exposure of the left coronary artery by medial sternotomy, it is necessary that the heart is rotated to the patient's right. This rotation the heart is generally conducted by inserting a gauze pad at the posterior surface of the heart. However, it is difficult with this technique to obtain excellent exposure of the target coronary artery because degree of the rotation is not controlled. Furthermore, sudden reduction in blood pressure may occur when the surgeon raise the heart to make a space for inserting the gauze pad.

In OPCAB and MIDCAB procedures, the surgeon has to perform the anastomosis in the time for which the blood flow of the target coronary artery can be stopped. A long time occlusion of the target coronary artery for the anastomosis gives the patient extremely dangerous conditions such an ventricular fibrillation or the like. Therefore, the surgeon tries to perform the anastomosis in a short time. This, however, may make unsuccessful anastomosis to invite occlusion of the bypass graft or coronary artery after the operation.

The stenosis at the point of hemostasis of the coronary artery for the anastomosis has often observed in the post-operative period. In order to interrupt the blood flow of the target coronary artery in the area to be anastomosed, the following technique has been generally used: to place a suture around the coronary artery proximal and/or distal to the site of the anastomosis; pass each end of the suture through the passage of a tube; and slide the tube down while pulling up each end of the suture just to the point of hemostasis. However, Endo at. al. report in The Japanese Journal of Thoracic Surgery, Vol. 51, No. 8, page 704 that the post operative cc:lusiom was observed at the point of hemostasis of the coronary artery because the coronary artery would be damaged by receiving overload force to compress the coronary artery. In fact, the force t o compress the coronary artery is not able to be under control according to this technique.

For such a case, in some proposals a flexible and elastic suture made of polyurethane or porous Tefron was used with the purpose of reducing the force applied to the coronary artery, or a Silastic tape was used for wide contact area with the surface of the coronary artery to compress the coronary artery gently. Nevertheless, as a fact, the stenosis or occlusion in the postoperative period has been often observed yet.

In order to reduce the force applied to the coronary artery, the technique of passing the suture through surrounding tissue of the coronary artery has been proposed. The tissue would play a part of a cushion against the force of compression. However, since a needle was used for passing the suture through the tissue around the coronary artery, the coronary artery itself may be injured with the needle. Further, this technique makes the compression force uncertain to occlude the target coronary artery.

An object of the present invention is to provide a device for safely and reliably carrying out OPCAB and MIDCAB.

Another object of the present invention is to prov,te a device used in OPCAB and MIDCAB procedures, which stabilizes anastomosis area without decrease of cardiac output.

Another object of the present invention is to provide a means used in OPCAB and MIDCAB procedures, for obtaining excellent exposure of a target coronary artery to be anastomosed without decrease of cardiac output.

Another object of the present invention is to provide a means used in OPCAB and MIDCAB procedures, which provides a blood flow to the distal myocardium during the anastomosis of a bypass graft to the target coronary artery.

Another object of the present invention is to provide a means used in OPCAB and MIDCAB, which controls a load force to compress the target coronary artery at a minimum load to stop a blood flow.

SUMMARY OF THE INVENTION

The present invention lies in a device for beating coronary artery bypass grafting on a beating heart, used for performing anastmosis of a bypass graft to a coronary art which device comprises:
- a means for rotating a heart for obtaining good exposure of the coronary artery and absorbing motion of the beating heart to provide motion reduction of an area of performing the anastomosis;
- a means for providing blood flow to the distal myocardium during the anastomosis of the bypass graft; and a means for compressing the coronary artery to perform proximal and distal occlusion of anastomosis portion, to stop blood flow through the coronary artery to provide a bloodless operative field during the anastomosis of the bypass graft.

BRIEF DESCRIPTION OF THE DRAWINGS

FIGS. 8(a) to 8(c) are each a drawing showing an example of the occluder of the present invention, and 8(a) is a sectional view of the occluder and 8(b) and 8(c) are each a perspective view of the shape of the front end of the occluder.

The numerals in the above drawings refer to the followings.

1: coronary artery; 2: aorta; 3: stenosis; 4: heart; 5: bypass graft; 7: left coronary artery; 8: stabilizer; 11: pad; 12: ribbon; 13: hole; 14: sealed part; 15: port; 16: fluid tube; 17: three-way stopcock; 18: syringe; 19: connector; 20: perfusion catheter; 22: connector; 23: insertion part; 24: trunk part; 25: connection part; 26: tip; 28: rib; 29: side passage; 30: occluder; 31: tube; 32: front stopper; 33: spring; 34: cylinder; 35: ring-shaped member; 36: back stopper; 37: cap; 38: wire; 39: loop; 41: suture; 42: pledget; 43: suture; 44: needle

DETAILED DESCRIPTION OF THE INVENTION

The present invention is described specifically below while referring to the accompanying drawings.

The present invention is constituted by three elements, that is, a fluid type pad (11), a perfusion catheter (20) and an occluder (30), and shows the maximum effect when all the elements are used. Two or one element may be used selectively. Explanation is made on each element below.

Pad

Figure 2:
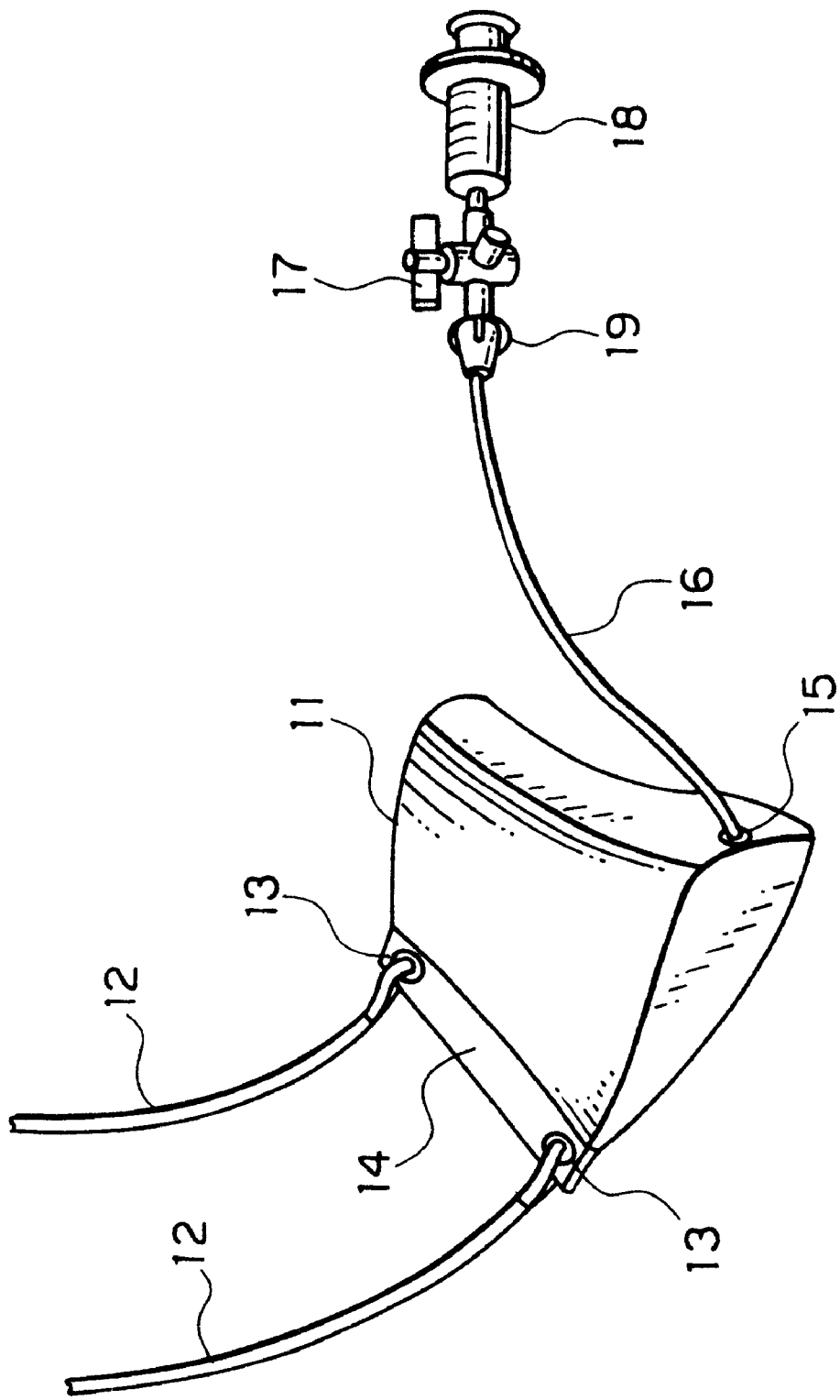
FIG. 2 is a drawing showing an example of the pad of the present invention.

The pad (11) shown in FIG. 2 has a sealed part (14) at one side; a hole (13) is formed at each end of the sealed part (14); and a ribbon (12) is inserted into each hole (13). While using the pad, the other ends of the ribbons (12) are fixed at the outside of the operative field to prevert: the pad from moving to an undesirable due to the beating heart. In the present example, two holes are formed, but the number of holes is not restricted to two. The ribbons (12) for fixation of the pad are not necessary depending upon the site at which the pad is located. In such a case, the sealed part (14) or the holes (13) are not required.

Figure 3:
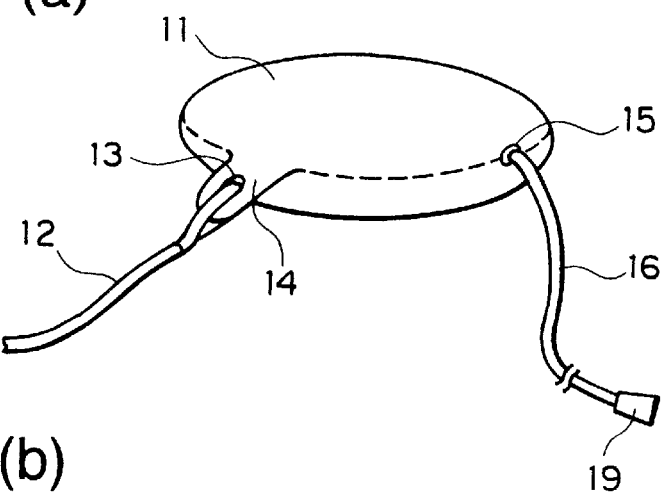
FIGS. 3(a) to 3(c) are each a drawing showing another example of the pad of the present invention.
Figure 3:
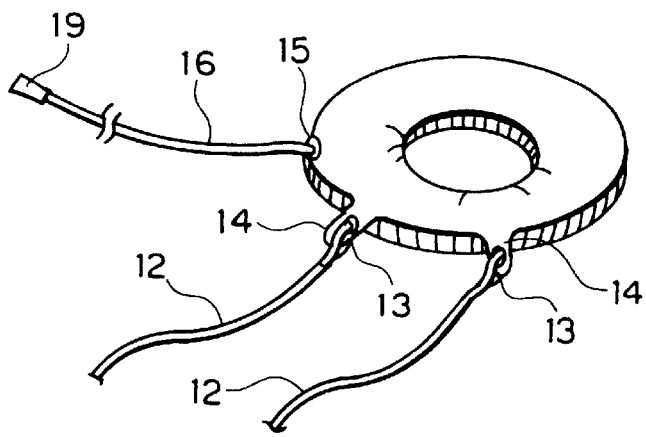
Figure 3:
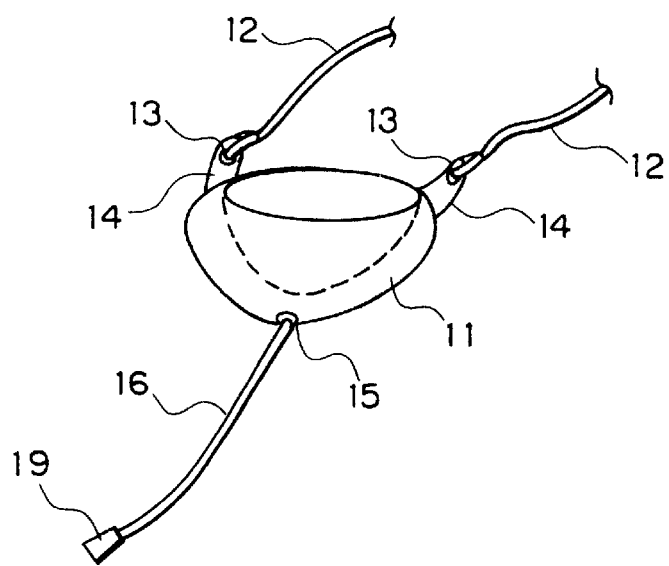

The pad (11) shown in the present example has a tetragonal shape. However, the shape of the pad is not restricted thereto and, as shown in FIGS. 3(a) to 3(c), various shapes such as circular shape, oval shape, floating ring shape, concave shape capable of covering the apex cordis of a heart, and the like can be employed depending upon the site at which the pad is located.

The pad (11) has a port (15), and one end of a fluid tube (16) is connected to the port (15). A fluid is introduced into the inside of the pad (11) by a syringe (18) through the fluid tube (16) to inflate the pad (11). The connection of the syringe (18) and the fluid tube (16) is made via a connector (19)provided at the other end of the fluid tube (16). Between the connector (19) and the syringe (18; is provided a three-way stopcock (17). By closing the throe-way stopcock (17), a fluid is held inside the pad (11).

The pad used in the present invention is made of a stretchable flexible material and has a thickness of preferably 0.05 to 0.50 mm. A thickness smaller than 0.05 mm is not preferred because damage such as pinhole or the like may appear during the use of the pad. The thickness larger than 0.50 mm is not preferred because the pad has neither stretchability nor flexibility to absorb the motion of the heart beating for stabilizing the anastomosis area.

The material for the pad used in the present invention is preferred to have a tensile elongation of at least 300% and a 100% modulus of 5 to 30 kg/cm². Herein, "tensile elongation" and "100% modulus" refer to values measured according to JIS K 6301. In the case that the tensile elongation is smaller than 300%, the pad is too hard and too inflexible to absorb the motion of the myocardium for stabilizing the anastomosis area. A 100% modulus smaller than 5 kg/cm² is not preferred because the pad is too soft and has no structural strength; a 100% modulus larger than 30 kg/cm² is not preferred because the pad is too hard and too inflexible to absorb the motion of the myocardium for stabilizing the anstomosis area. There is no particular restriction as to the kind of the material as long as there is used a material satisfying the above requirements. Referred as the material are, for example, soft polyvinyl chloride, polyurethane, polyester, polyamide, silicone rubber, polyolefin, natural rubber, synthetic rubbers, and polymer alloys or laminates thereof.

A following technique using the pad is explained to clarify effects of the present invention, with reference to FIG. 1 and FIGS. 4(a) to 4(c).

Figure 4:
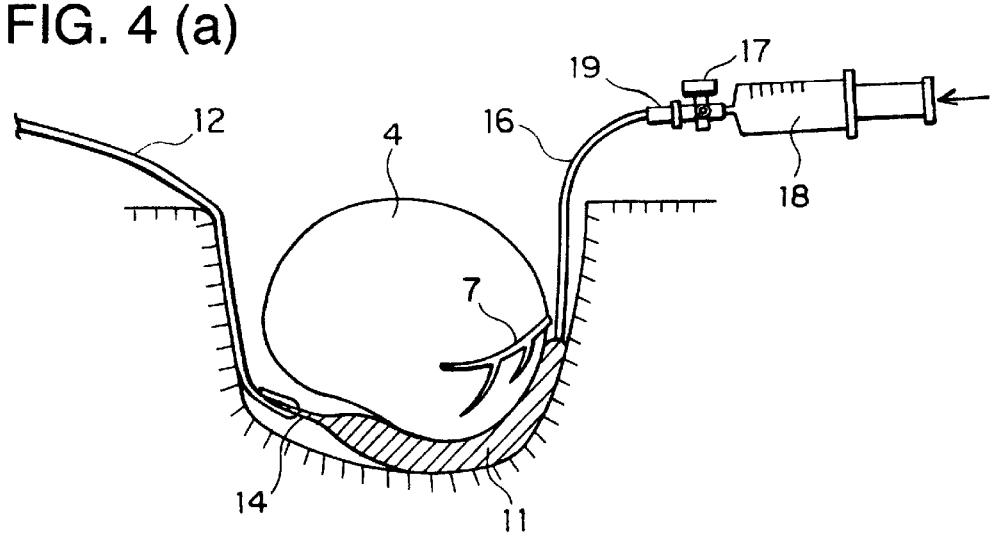
FIGS. 4(a) to 4(c) are drawings showing a way in which the pad of the present invention is used, wherein a heart is looked at from the apex cordis.
Figure 4:
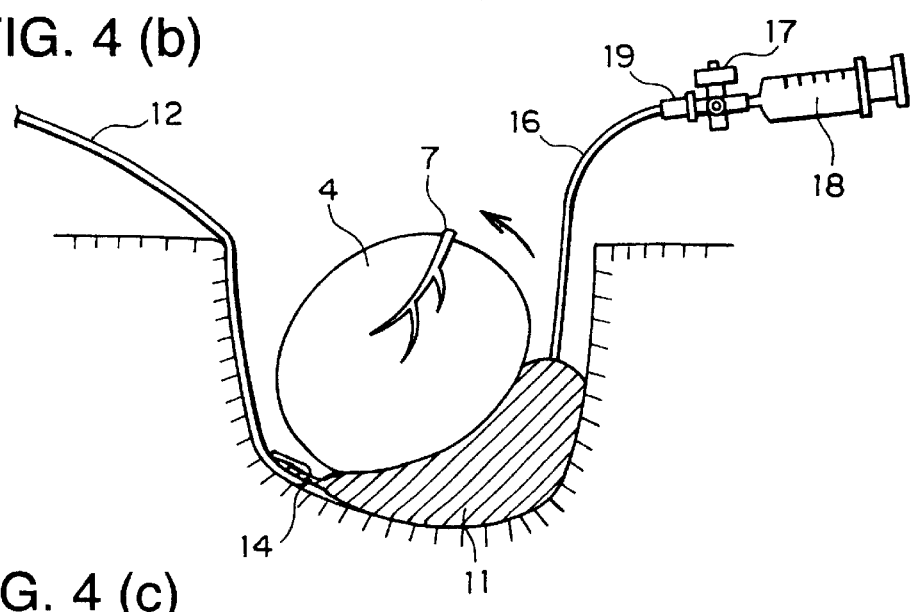
Figure 4:
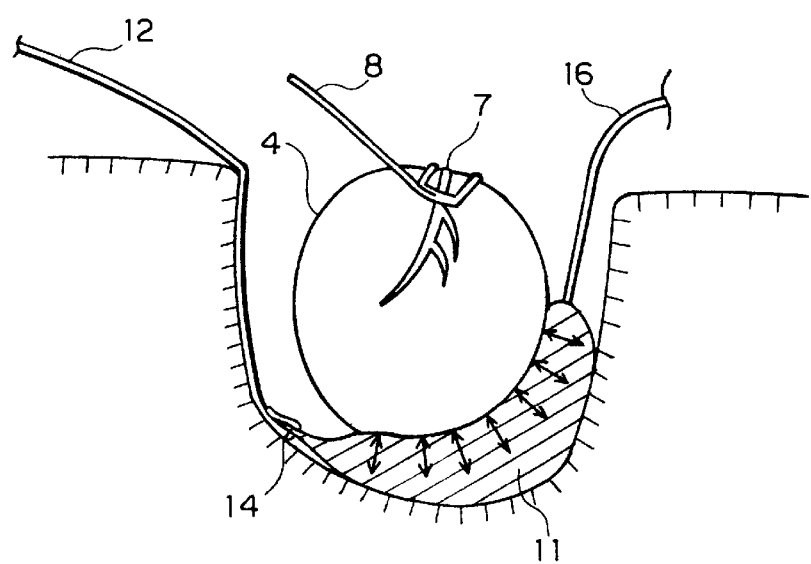
Figure 5:
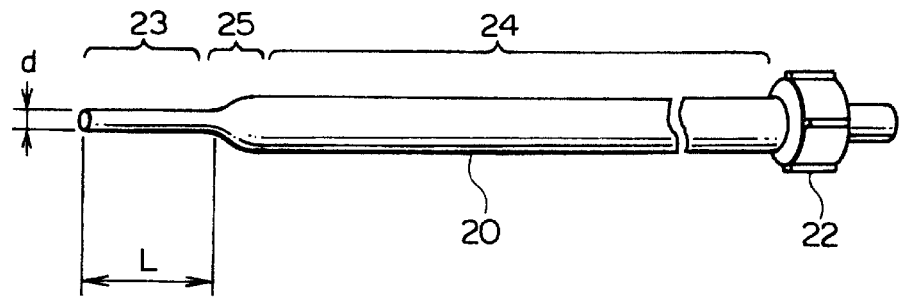
FIG. 5 is a drawing showing arc example of the perfusion catheter of the present invention.

Illustrated is a heart having a stenosis (3) at the upstream site of a left coronary artery (7). The anastomosis of a bypass graft at the downstream site in being performed for providing blood flow to the distal myocardium. When medial sternotomy is used, the surgeon is unable to obtain good exposure of the target left coronary artery (7) because it is located at the left to posterior surface of the patient's heart as shown in FIG. 4(a).

In order to obtain excellent exposure of the target coronary artery (7) to be anastomosed, the pad having a shape shown in FIG. 2 is used. The pad (11) is inserted at the posterior surface of the heart as shown in FIG. 4(a) and fixed by holding ribbons (12) at the outsides of the operative field. A fluid is gradually introduced into the inside of the pad (11) using syringe (18); thereby, the pad is inflated slowly so as to rotate the heart to the patient's right as shown in FIG. 4(b). With this pad of the present invention, t surgeon is an,(e to obtain excellent exposure of the target left coronary artery (7) because it in possible to adjust the heart rotation under control of volume of fluid introduced into the pad.

Heart rotation must be conducted slowly while observing changes of the patient's hemodynamics such as blood pressure, or electrocardiogram. Rapid rotation must be avoided because it provides the heart with sudden increase of load to reduce blood pressure. According to the present invention, however, in the case that blood pressure is reduced in the step of heart rotation, it can be recovered easily by immediate deflation of the pad (11) to release load applied to the heart. As soon as the recovery of the blood pressure has been confirmed, the heart can be carefully rotated again.

Figure 1:
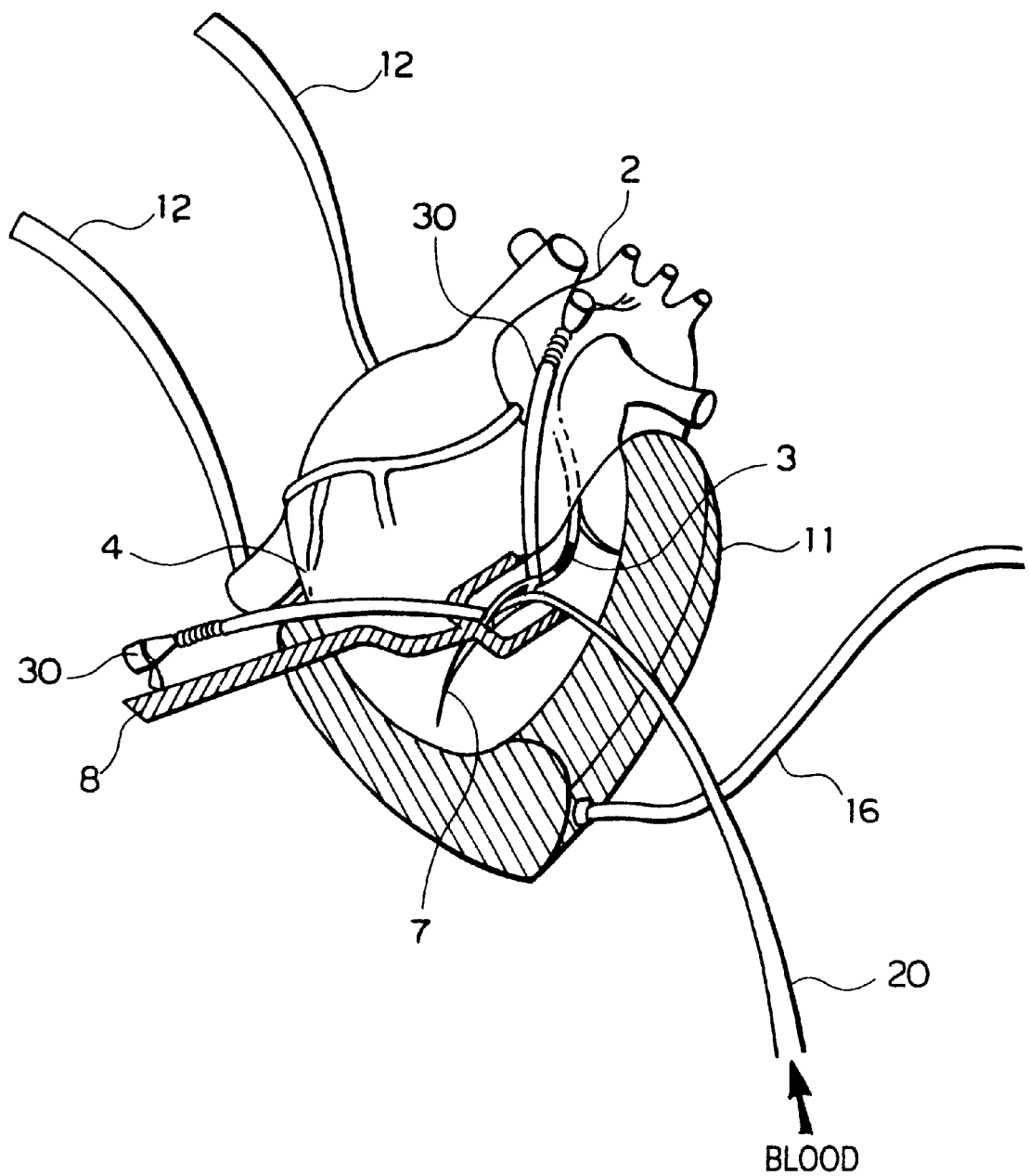
FIG. 1 is a drawing showing a state in which OPCAB is being carried out using the device for CABG on the beating heart, of the present invention.

In order to stabilize the anastomosis area of the heart, the stabilizer described in the background art is used in combination with the pad of the present invention. The stabilizer (8) has two fork-shaped legs at the front end as shown in FIG. 1. The two legs compress the anastomosis area and restrict the motion of the myocardium. Though many types of stabilizers are commercially available, a proper stabilizer is selected depending upon operative procedure. According to the technique using the pad of the present invention, following effects are expected even if any type of stabilizer is used.

The pad (11) is able to deform flexibly in response to the heart beating to absorb the motion of the myocardium because it is freely stretchable and highly flexible. As shown in FIG. 4(c), while the stabilizer provides the target area with motion reduction in the X and Y plains, the pad (11) provides target area with motion reduction in the Z plain without reducing stroke due to direct ventricular compression by the stabilizer. In comparison with the case using the stabilizer alone, this technique provides not only excellent stable state of the anastomosis area but also less restriction of the myocardial motion. Therefore, this invention is useful for a means to stabilize the anastomosis area without increasing load provided to the heart and to obtain excellent exposure of the target coronary artery to be anastomosed.

Perfusion catheter

The perfusion catheter (20) is made of a flexible material and is constituted by three parts, that is, an insertion part (23) of small diameter to be inserted into a target coronary artery anastomosed, a trunk part (24) of large diameter and a connection part (25) which connects the insertion part (23) to the trunk part (24). Inner diameter and outer diameter of the connection part (25) gradually decrease in a direction proceeding from the trunk part (24) toward the insertion part (23) to connect the connection part (25) with the insertion part (23). Smooth surface is formed at the point of connection between the connection part (25) and the insertion part (23), and between the connection part (25) and the trunk part (24). The insertion part (23) has a proper outer diameter fitted for inner diameter of the coronary artery to be inserted. For example, the outer diameter is preferably 0.7 to 1.5 mm for left anterior descending artery. Of course, the outer diameter may be changed according to the inner diameter of the coronary artery to be inserted.

According to this invention, 2d<D must be satisfied, where D is inner diameter of the trunk part (24) and d is inner diameter of the insertion part (23). 2d>D is not preferred because it provides lower pressure from the blood flow at the outlet of the perfusion catheter (20) and no sufficient blood flow to the distal myocardium. The length L of the insertion part (23) is preferably in a range of 10d to 35d. A length smaller than 10d is not preferred because the length is not sufficient for insertion into the target coronary artery and fixation of the insertion part. A length larger than 35d is not preferred because the pressure loss of the blood flow through the insertion part (23) is larger and provides no sufficient blood flow to the distal myocardium. Lager loss in the pressure from the blood flow through the perfusion catheter (20) provides hemolysis causing complications such as renal diseases and the like.

The perfusion catheter (20) is manufactured in the process including drawing which is carried out under given conditions. In the drawing process, one end of a flexible tube is drawn under the following equation:

$$D/T = d/t$$

where T is the wall thickness of the trunk part (24) and t is the wall thickness of the insertion part (23).

A connector (22) is prepared at the proximal end of the perfusion catheter (20) for connection with resources of the blood flow such as blood pump or the like. Though any kind of the connector can be used for the perfusion catheter, a connector with rotating lure is preferred because connection can be hold against the pressure from the blood flow through the perfusion catheter.

The perfusion catheter is preferably formed from flexible thermoplastics having a hardness of 50 shore A or more for good kink resistance. A thermoplastic elastomer composed of soft segment and hard segment is preferred. For example, polyamide elastomers, polyester elastomers, polyolefin elastorners, polyurethane elastomers, and polymer alloys thereof can be used, however, the present invention is not restricted thereto.

Figure 7:
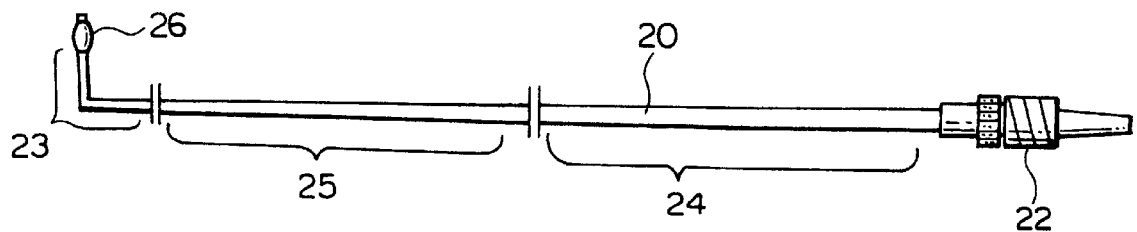
FIG. 7 is a drawing showing another example of the perfusion catheter of the present invention.

A crooked shape of the distal end of the perfusion catheter (20) may be formed as shown in FIG. 7. The perfusion catheter (20) having the crooked shape allows visualization for suturing behind the perfusion catheter (20) to be inserted into the coronary artery (7). The crooked shape also makes handling of the perfusion catheter (20) easy in the operative field, however, the blood flow rate is reduced slightly.

A length between the distal end and the crooked point is preferably 5 to 20 mm. In the case of the length smaller than 5 mm, the distal end of the perfusion catheter comes out of the coronary artery during perfusion because deep insertion cannot be carried out. In the case of the length larger than 20 mm, the whole length from the distal and to the crooked point cannot be inserted into the coronary artery and the crooked point positioned outside the coronary artery interrupts visualization for suturing behind the perfusion catheter (20)."

The distal end of the perfusion catheter (20) may be crooked at the angle determined depending upon the site of the coronary artery into which the perfusion catheter is inserted. According to the present invention, the angle in the range from 80 to 100 degrees is preferred. The angle out of the above range is not preferred because the perfusion catheter (20) interrupts visualization for suturing.

Figure 6:
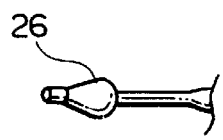
FIGS. 6(a) to 6(c) are each a drawing showing an example of the shape of the tip attached at the distal end of the perfusion catheter of the present invention, and 6(a) and 6(b) are each a perspective view and 6(c) is a sectional view.
Figure 6:
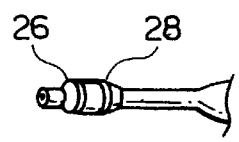
Figure 6:
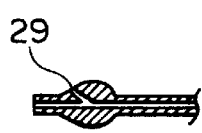

A tip (26) may be attached at the distal end of the perfusion catheter (20). The tip (26) prevents the perfusion catheter (20) from coming out of the coronary artery due to the pressure of the blood flow through the perfusion catheter. The tip (26) also performs complete plugging of the coronary artery. The shape of the tip is not restricted. For example, a spindle shape as shown in FIG. 6(a), or an egg shape as shown in FIG. 6(b) may be used. As shown in FIG. 6(b), ribs (28) may be also formed on the surface of the tip for higher resistance to disconnection from the coronary artery. Of course the present invention is not restricted to this shape.

A side passage (29) may be formed at the distal end of the perfusion catheter (20) as shown in FIG. 6(c) for maintaining the blood flow in the case that no sufficient blood flow is obtained because the opening at the distal end of the perfusion catheter (20) is in contact with the inner wall of the coronary artery.

The tip (26) is preferably formed from flexible thermoplastics having a hardness of 30 to 100 Shore A for plugging the coronary artery without providing any load thereto. A hardness smaller than 30 Shore A is not preferred because the tip (26) breaks easily during the use. Fragments of the broken tip remain in the coronary artery to occlude in the postoperative period. A hardness larger than 100 Shore A is not preferred because the tip (26) is so hard. The coronary artery may be damaged by inserting the hard tip into the coronary artery. There is no restriction as to the kind of the material as long as the above requirements are satisfied. For example, silicone rubber, polyamide elastomers, polyester elastomers, polyolefin elastomers, polyurethane elastomers, and polymer alloys thereof can be used for this invention.

A following technique using the perfusion catheter is explained to clarify effects of the present invention, with reference to FIGS. 10(a) to 10(d).

Figure 10:
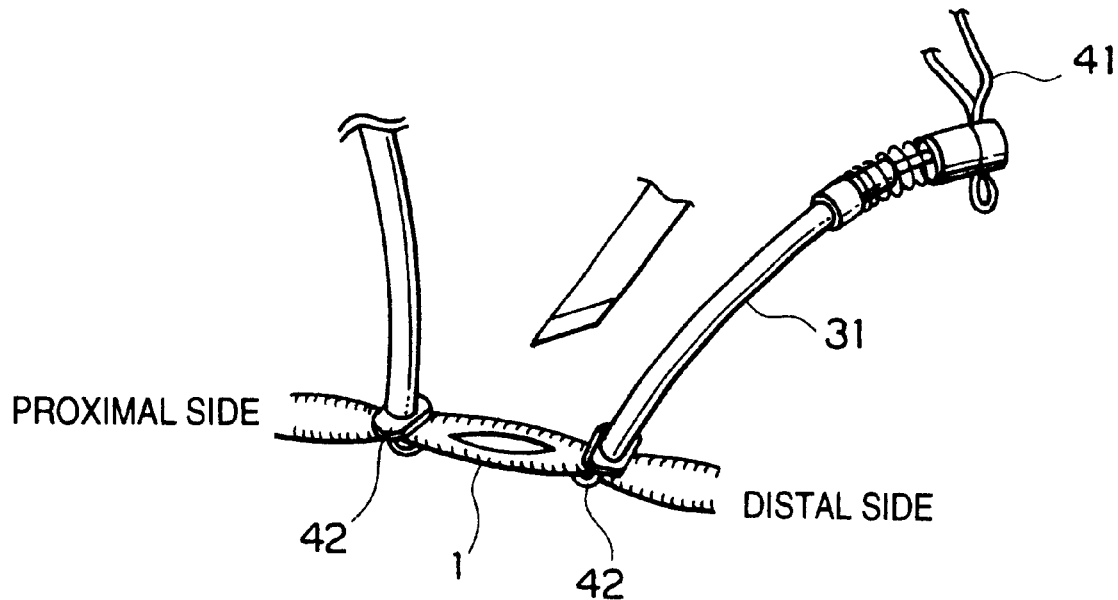
FIGS. 10(a) to 10(d) are drawings showing a way in which a perfusion catheter is fixed to an coronary artery using the occluder of the present invention.
Figure 10:
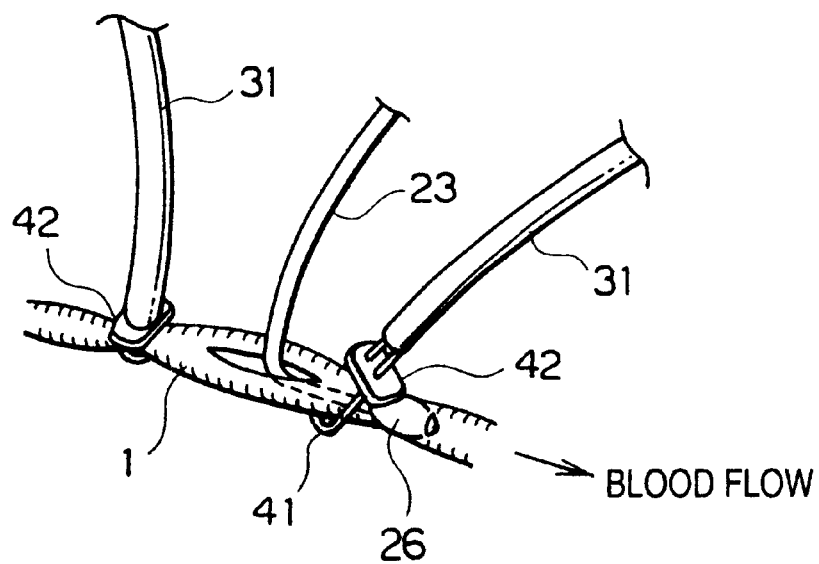
Figure 10:
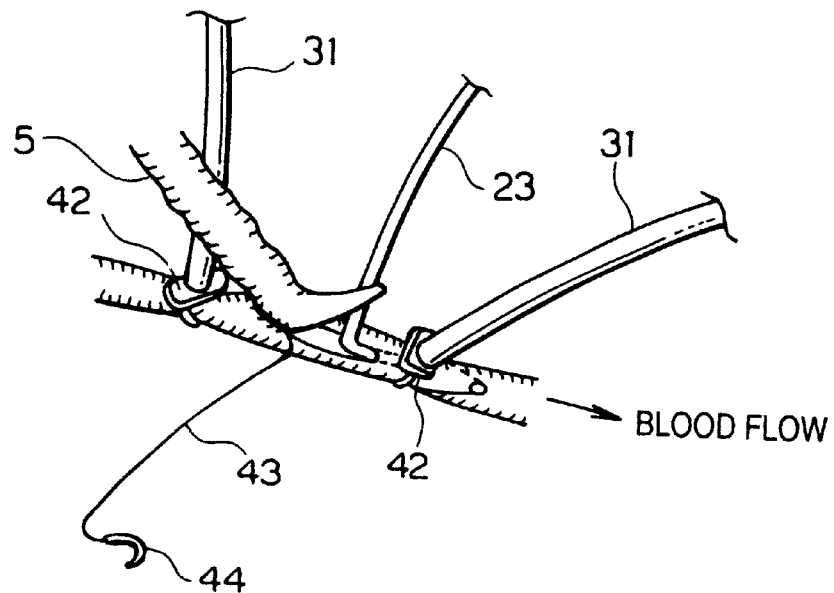
Figure 10:
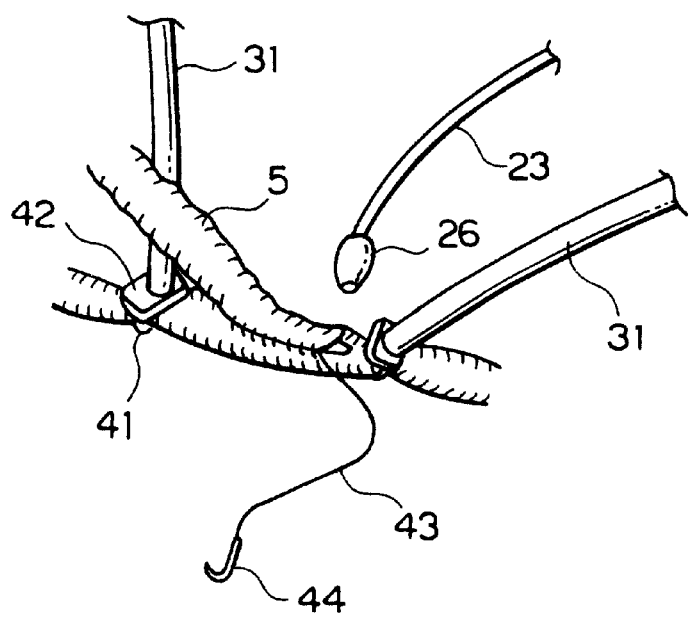

As shown in FIG. 10(a), a suture (41) with a pledget (42) is placed around the coronary artery proximal and distal to the site of the anastomosis to be tightened for stopping the blood flow through the coronary artery and arteriotomy is carried out. Following arteriotomy, as shown in FIG. 10(b), the distal suture is slightly loosed and the distal end of the perfusion catheter (20) is inserted into the distal coronary artery. The tip (26) is inserted beyond the point of the suture placement Successfully, then the suture is gently applied at the back and of the tip (26) to fix the perfusion catheter (20). After the insertion, the connector (22) of the perfusion catheter (20) is connected to a resource of the blood flow which has been placed at the femoral artery. The distal coronary artery as perfused through the perfusion catheter (20) depending upon blood pressure of the femoral artery. For occlusion of the coronary artery and fixation of the perfusion catheter, use of an occluder to be described later is preferred because of no damaging of the coronary artery.

As shown in FIG. 10(c), the bypass graft (5) is anastomosed to the coronary artery (1) under perfusion to the distal coronary artery. The perfusion catheter maintains the blood flow to the distal coronary artery and prevents myocardial ischemia during the anastomosis. According to the present invention, it is possible to take a sufficient time for the anastomosis, and the surgeon is able to perform the anastomosis safely and completely.

Right before suturing is secured, the perfusion catheter is removed as shown in FIG. 10(d). As described above, it is clear that the perfusion catheter of the present invention is useful for OPCAB or MIDCAB procedure as a means for perfusion to the distal myocardium during the anastomosis of the bypass graft to the coronary artery.

Occluder

A cylinder (34) is inserted into the passage of a tube (31) at the back end, and fixed. A ring-shaped member (35) is inserted into the passage of the cylinder (34). The ring-shaped member (35) is held in such a state that it can slide in the passage of the cylinder (34) in the lengthwise direction of the cylinder. A back stopper (36) is provided on the circumference of the back end of the ring-shaped member (35), and a front stopper (32) is provided on the circumference of a tube site near the back end of the tube (31). A spring (33) is provided between the front stopper (32) and the back stopper (36). The two ends of the spring (33) are fixed to the front stopper (32) and the back stopper (36). Thus, the ring-shaped member (35) is fixed to the tube (31) via the spring (33); and the range in which the ring-shaped member (35) can slide in the lengthwise direction of the cylinder (34), is restricted by the length and elastic deformation range of the spring. The front stopper (32) and the back stopper (36) have been described here in order to explain a means for fixing the spring (33); however, the means for fixing the spring (33) is not restricted thereto and, depending upon the fixation means employed, it is not necessary to provide the front stopper (32) and the back stopper (36).

To the back stopper (36) may be fitted a cap (37) engageable to the ring-shaped member (35). The function of the cap (37) is described later at a section regarding the way on use of an occluder.

In the present example (FIG. 8(a)), a cylinder (34) and a ring-shaped member (35) are located in the passage of a tube (31). However, it is possible that the cylinder (34) is fixed on the circumference of the tube (31) and the ring-shaped member (35) is fixed on the circumference of the cylinder (34). In this case as well, the ring-shaped member (35) is fixed to the tube (31) via a spring (33) and the ring-shaped member (35) is slidable in the lengthwise direction of the tube (31).

The tube (31) must be made of a flexible material and must have appropriate strength and flexibility. Any material is used as long as it satisfies the above requirements. There can be used, for example, polyvinyl chloride, polyurethane, silicone, polyamide, polyester, polyolefin, polytetrafluoroethylene, copolymers or polymer alloys thereof, natural rubber and synthetic rubbers.

The front end of the tube (31) can be formed simply by cutting the tube so that the cross section formed by the cutting becomes perpendicular to the lengthwise direction of the tube. Preferably, the edge of the front end is rounded so that the front end gives no damage to the coronary artery. More preferably, as shown in FIGS. 8(b) and 8(c), the front end is squeezed inwardly, or a ring-shaped member is fitted to the front end so that the front end can have a larger contact area. With this enlarged contact area, the stress applied to the coronary artery when the coronary artery is compressed and blood flow is stopped, can be dispersed; and the probability of coronary artery damaging can be reduced.

In the present invention, the static friction coefficient $\mu$ between the ring-shaped member (35) and the cylinder (34) is preferably 1.0 or less. Herein, "static friction coefficient $\mu$" is a frictional resistance at which an object made of a material A, placed on a slope made of a material B begins to slide when the inclination angle $\theta$ of the slope is gradually increased, and is a value represented by $\mu = \tan\theta$. A static friction coefficient larger than 1.0 is not preferred because the slidability of the ring-shaped member (35) is lower and the quantitative control of the force applied for compressing of the coronary artery is impossible.

As long as the static friction coefficient between the ring-shaped member (35) and the cylinder (34) is 1.0 or less, there is no particular restriction as to the kinds of the materials for the above two constituent members. There can he preferably used, for example, a combination of two stainless steels, or a stainless steel and a polytetrafluoroethylene, or two polytetrafluoro-ethylene. Alternatively, a fluororesin or a p-xylylene resin may be coated on the surfaces of the cylinder (34) and the ring-shaped member (35) for obtaining higher surface lubricity.

In the present example, slidability is secured by using the cylinder (34). However, the cylinder (34) may be omitted when the tube (31) per se can satisfy the above-mentioned requirements for the cylinder. The objects of the present invention can be achieved also when the cylinder (34) and the ring-shaped member (35) are omitted and only a spring is provided at the back end of the flexible tube (31); however, since with no use of the ring-shaped member (35), deflection appears when the spring (33) is compressed, making it difficult to control the tension applied to the blood vessel, it is preferred to use these members.

In the present invention, a spring is used as a source which generates a stress necessary for compressing of a coronary artery and resultant stoppage of blood flow. The spring (33) has a compression spring constant of preferably 0.001 to 0.015 kgf/mm. A compression spring constant smaller than 0.001 kgf/mm is not preferred because no stress sufficient for compressing of the coronary artery and stoppage of blood flow is obtained. A compression spring constant larger than 0.015 kgf/mm is not preferred because fine adjustment of the stress required for compressing of the coronary artery is impossible and, moreover, too high a stress may be applied, which may incur damaging of the coronary artery.

In the present invention, the stress generated when the spring is compressed completely, that is, the highest generatable stress is preferably not higher than 200 g and is preferably in a range of 80 to 160 gf. Compressing the coronary artery at a stress larger than 200 gf is not preferred because it may invite damaging of the coronary artery. A generatable stress smaller than 80 g is not preferred because even complete compression of the spring may not be able to occlude the coronary artery. A minimum required stress should be applied for occlusion with no damaging of the coronary artery, and a generatable stress higher than 160 gf is not preferred because the coronary artery may receive excessive stress.

There is no restriction as to the material for the spring (33) as long as the above requirements are satisfied. There can be used a spring made of a metal (e.q. stainless steel), a plastic or a rubber; or an air type sprtnc.

Figure 9:
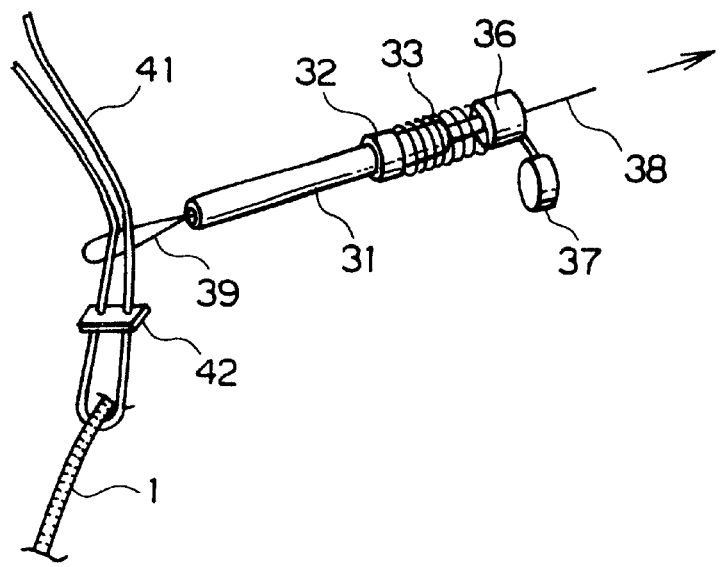
FIGS. 9(a) to 9(c) are drawings showing a way in which the occluder of the present invention is used.
Figure 9:
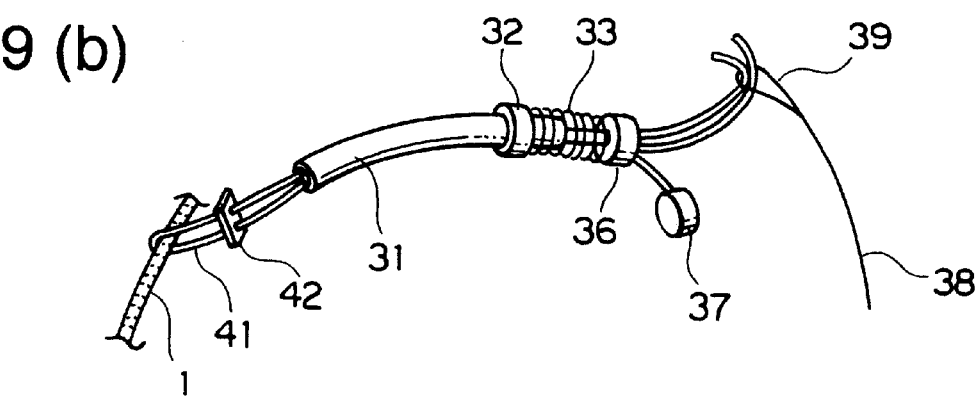
Figure 9:
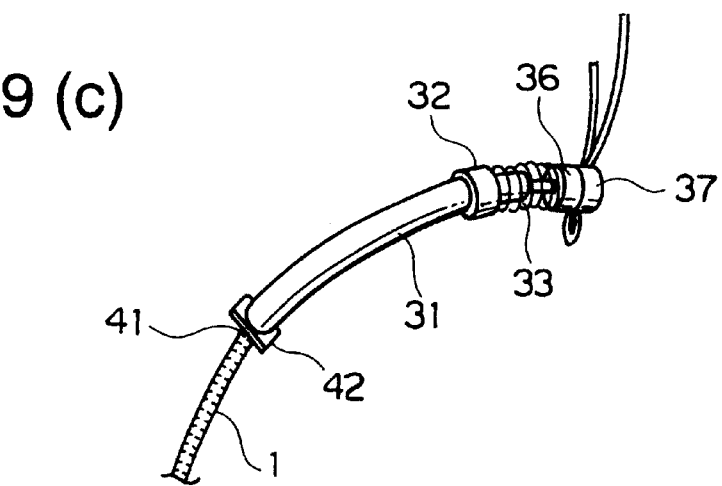

Next, description is made on the way in which the occluder of the present invention as used, referring to FIGS. 9(a) to 9(c), and the effects of the present invention are clarified. Further, an auxiliary device used together with the occluder is described.

The auxiliary device is formed from a wire (38) having a loop (39) at the front end, and is beforehand passed through the passages of the tube (31), cylinder (34) and ring-shaped member (35) of the occluder. At this time, the loop (39) is held in a state that it is projected from the front end of the tube (31).

Preferably, the loop (39) and the wire (38) show neither breakage nor elongation larger than 10% when a tensile stress of 1 kgf or more is applied thereto, because such breakage or tensile elongation may make impossible that the suture (41) is passed through the passage of the occluder in the technique later described. There is no particular restriction as to the materials for the loop (39) and the wire (38) as long as the above-mentioned requirements are satisfied. There can be used preferably, for example, a metal wire, a polyamide fiber, or a polyester fiber.

The following technique is used for the occluder of the present invention: the suture (41) is placed around the target coronary artery (1) proximal and distal to the site of the anastomosis; the both ends of the suture (41) are passed through a pledget (42) made of Tefron, then put into the loop (39) as shown in FIG. 9(a); the suture (41) is passed through by pulling the wire out of the passage of the occluder as shown in FIG. 9(b); while pulling up ends of the suture through the passage of the occluder, the occluder with pledget (42) is slid down just to the point of hemostasis to compress the coronary artery; the suture (41) is interposed between the cap (37) and the ringshaped member (35) to maintain the occlusion as shown in FIG. 9(c). Other methods for fixing the suture can be applied for the occluder of the present invention.

The pledget (42) prevents direct contact of the front end of the tube (31) with coronary artery (1) and protects the coronary artery. A nonwoven fabric, a porous material such as sponge, or a sheet formed from polyurethane or silicone rubber is preferably used for the pledget. Though there is no restriction as to the suture (41), an elastic suture made of polyurethane or a Gore-tex suture in preferred.

In the present invention, the force necessary for compressing coronary artery (1) can be set as desired by controlling the amount of slide of ring-shaped member (35). As the ring-shaped member (35) is forced deeper into the passage of the cylinder (34), the stress given by the spring (33) is larger and the compressing force becomes larger. However, the stress for compressing the coronary artery is not larger than said highest generatable stress.

The relationship between the amount of the slide and the stress given by the spring is in direct proportion and is determined by the above-mentioned spring constant of the spring. For example, a spring having a spring constant of 0.005 kgf/mm generates an stress of 0.005 kgf every time when the ring-shaped member (35) is inserted into the cylinder (34) by 1 mm. The stress of the spring is equal to the tension of the suture (41), that is, the stress for compressing the coronary artery (1). As clear from the above, the present invention can quantitatively control the force for compressing a coronary artery and can stop blood flow at a minimum required stress and, therefore, is very suitable as a means for occlusion of the coronary artery.

As clear from the above, the present invention includes a means for rotating a heart to obtain excellent exposure of the target coronary artery to be anastomosed without reducing cardiac output; a means for stabilizing the anastomosis area; a means for perfusion to the distal myocardium during the anastomisis of the bypass graft to the coronary artery; a means for controlling the force compressing the target coronary artery quantitatively for occlusion at a minimum stress, and is very useful for carrying out OPCAB and MIDCAB safely and completely.

INDUSTRIAL APPLICABILITY

The present invention is utilized as devices for carrying out anastomosis of the bypass graft to the coronary artery on the beating heart.

What is claimed is:

1. A device for coronary artery bypass grafting on a beating heart, used for performing anastomosis of a bypass graft to a coronary artery, which device comprises:
    a means for rotating a heart for obtaining good exposure of the coronary artery and absorbing motion of the beating heart to provide motion reduction of an area of performing the anastomosis;
    a means for providing blood flow to the distal myocardium during the anastomosis of the bypass graft;
    and a means for compressing the coronary artery to perform proximal and distal occlusion of anastomosis portion, to stop blood flow through the coronary artery to provide a bloodless operative field during the anastomosis of the bypass graft.

2. A device for coronary artery bypass grafting on a beating heart according to claim 1, wherein said means for rotating a heart for obtaining good exposure of the coronary artery and absorbing motion of the beating heart to provide motion reduction of an area of performing the anastomosis, is an inflatable pad formed from a freely stretchable and flexible material.

3. A device for coronary artery bypass grafting on a beating heart according to claim 1, wherein said means for providing blood flow to the distal myocardium during the anastomosis of the bypass graft is a perfusion catheter comprising:
    a trunk part having large inner and outer diameters; an insertion part having small inner and outer diameters, the inner diameter of said insertion part being ½ or less of the inner diameter of said trunk part, and the length of said insertion part being from 10 to 35 times the inner diameter of said insertion part; and
    a connection part gradually changing inner and outer diameters to connect said trunk part with said insertion part with no level difference between inner and outer surfaces of said trunk part or insertion part and those of said connection part.

4. A device for coronary artery bypass grafting on a beating heart according to claim 3, wherein said perfusion catheter has a tip at the distal end of the insertion part, and said tip is comprised of a flexible riesini having a durometer hardness of 30 to 100 shore.

5. A device for coronary artery bypass grafting on a beating heart according to claim 3 or 4, wherein said insertion part of said perfusion catheter has an angle.

6. A device for coronary artery bypass grafting on a beating heart according to claim 1, wherein said means for compressing the coronary artery to perform proximal and distal occlusion of anastomosis portion, to stop blood flow through the coronary artery to provide a bloodless operative field during the anastomosis of the bypass graft is an occluder comprising at least a flexible tube and a spring provided at rear end of said tube.

7. A device for coronary artery bypass grafting an a beating heart according to claim 6, wherein said occluder comprises a flexible tube; a ring-shaped member provided at the rear end of said flexible tube, said ring-shaped member being slidable to said flexible tube; and a spring provided at the rear end of said flexible tube, one end of said spring being fixed to said flexible tube and the other end thereof being fixed to said ring-shaped member.

8. A device for coronary artery bypass grafting on a beating heart according to claim 1, wherein said means for compressing the coronary artery to perform proximal and distal occlusion of anastomisis portion, to stop blood flow through the coronary artery to provide a bloodless operative filed during the anastomosis of the bypass graft comprises:
    a) at least an occluder, wherein the occluder comprises a flexible tube; a ring-shaped member provided at the rear end of said flexible tube, said ring-shaped member being slidable to said flexible tube; and a spring provided at the rear end of said flexible tube, one end of said spring being fixed to said flexible tube and the other end thereof being fixed to said ring-shaped member; and
    b) an auxiliary device for passing a thread through the passage of the occluder.

* * * * *